United States Patent [19]

MacDonald

[11] Patent Number: 5,786,364

[45] Date of Patent: Jul. 28, 1998

[54] BICYCLIC ISOTHIOUREA DERIVATIVES USEFUL IN THERAPY

[75] Inventor: James MacDonald, Pittsford, N.Y.

[73] Assignee: Astra Aktiebolag, Sodertalje, Sweden

[21] Appl. No.: 615,254

[22] PCT Filed: Feb. 9, 1996

[86] PCT No.: PCT/SE96/00162

§ 371 Date: Mar. 8, 1996

§ 102(e) Date: Mar. 8, 1996

[87] PCT Pub. No.: WO96/24588

PCT Pub. Date: Aug. 15, 1996

[30] Foreign Application Priority Data

Feb. 11, 1995 [GB] United Kingdom ............ 9502669
Feb. 11, 1995 [GB] United Kingdom ............ 9502670

[51] Int. Cl.[6] .................. C07D 217/02; C07C 335/02; A61K 31/47; A61K 31/155
[52] U.S. Cl. .................. 514/307; 546/145; 564/252; 514/631
[58] Field of Search .............. 546/145; 514/307, 514/631; 564/252

[56] References Cited

U.S. PATENT DOCUMENTS

| | | | |
|---|---|---|---|
| 3,847,934 | 11/1974 | Neumann et al. | 546/145 |
| 4,029,792 | 6/1977 | Danielewicz et al. | 424/251 |
| 4,211,867 | 7/1980 | Rasmussen | 544/60 |
| 5,223,498 | 6/1993 | Gopalan | 514/231.2 |

FOREIGN PATENT DOCUMENTS

| | | | |
|---|---|---|---|
| 0392802 | 4/1990 | European Pat. Off. | |
| 0411615 | 8/1990 | European Pat. Off. | |
| 1157626 | 6/1959 | Germany | |
| 1178242 | 1/1967 | United Kingdom | |
| 2020280 | 2/1979 | United Kingdom | 546/145 |
| 9412165 | 11/1993 | WIPO | |
| 9505363 | 8/1994 | WIPO | |
| 9509619 | 10/1994 | WIPO | |

OTHER PUBLICATIONS

U. Förstermann et al. "Induced RAW264.7 macrophages express . . . " Eur. J. Pharmacology (1992) 225: 161–165.

D. Bredt et al. "Isolation of nitric oxide synthetase. . . . " Proc. Natl. Acad. Sci. USA (1990) 87: 68–685.

C.R. Rasmussen et al. "A versatile synthesis of novel . . . " Synthesis (1988) 6: 460–466.

J.S. Pollock et al. "Purification and characterization of particulate . . . " Proc. Natl. Sci. USA (1981) 88: 1048–10484.

H.J. May: "Zur Synthese von N–(2–Imidazolin–2–yl)–N–(4–indanyl)amin(In danazolin)." IArzeneimittel Forschung Drug Research., vol. 30, No. 10, 1980, pp. 1733–1737.

Primary Examiner—Zinna Northington Davis
Attorney, Agent, or Firm—Nixon & Vanderhye

[57] ABSTRACT

There are provided novel compounds of formula I

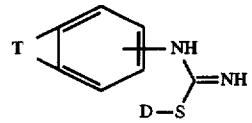

wherein
D represents alkyl C1 to 6;
T represents a $C_{3-5}$ saturated or unsaturated alkylene chain substituted by —$(CH_2)_m$—NXY; —O—$(CH_2)_2$—NH— substituted by —$(CH_2)_m$—NXY; or —U—$(CH_2)_a$—N(X)—$(CH_2)_b$—;

and a, b, m, X and Y are as defined in the specification together with processes for their preparation, compositions containing them and their use in therapy. Compounds of formula I are expected to be useful inter alia in the treatment of neurodegenerative disorders.

11 Claims, No Drawings

BICYCLIC ISOTHIOUREA DERIVATIVES USEFUL IN THERAPY

This application is a 371 of PCT/SE96/00162, filed Feb. 9, 1996.

This invention relates to novel compounds, processes for their preparation, compositions containing them and their use as neuroprotective agents.

Thiourea and isothiourea derivatives have been described before for a variety of therapeutic uses. WO 94112165 (Wellcome) describes simple isothiourea derivatives for use in the treatment of inter alia systemic hypotension, septic shock and inflammatory conditions; WO 95/09619 (Wellcome) (published after the priority date of this application) describes substituted urea and isothiourea derivatives for use in the treatment of cerebral ischaemia; United Kingdom Patent No 1178242 (Wellcome) discloses bisisothioureas having anti-inflammatory activity; European Patent Application No 411615 (Warner Lambert) discloses thiourea derivatives having use in the treatment of symptoms of cognitive decline; European Patent Application No 392802 (Beecham) discloses thiourea derivatives for use in the treatment of bronchial, cerebrovascular or neuronal disorders.

Isothiourea derivatives are also known as chemical intermediates in the preparation of guanidine derivatives (see U.S. Pat. No. 4,211,867 (McNeil Laboratories) and Synthesis (1988) 6, 460–466 (Rasmussen) which disclose the compound 4-dimethylaminophenylcarbamimidothioic acid methyl ester and U.S. Pat. No. 5,223,498 (Boots).

N-Alkoxyphenyl-N'-quinolinyl-thiourea derivatives useful as tuberculostatic agents are disclosed in DE-B-1157626 (Hoechst).

International Patent Application WO 95/05363 (Fisons) (published after the priority date of this application) discloses N-phenyl amidine derivatives which are indicated for the treatment of inter alia neurodegenerative disease.

We have now discovered a new and useful group of isothiourea derivatives.

According to the invention, there are provided compounds of formula I

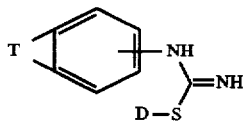

wherein

D represents alkyl C1 to 6

T represents a $C_{3-5}$ saturated or unsaturated alkylene chain substituted by $—(CH_2)_m—NXY$; $—O—(CH_2)_2—NH—$ substituted by $—(CH_2)_m—NXY$; or $—U—(CH_2)_a—N(X)—(CH_2)_b—$;

U represents NH, O or $CH_2$;

a and b, which may be the same or different, represent an integer 0 to 3, provided that a+b is in the range 1 to 3;

X and Y, which may be the same or different, represent hydrogen, alkyl C1 to 6, or a group $—(CH_2)_nQ$, or NXY together represents piperidinyl, pyrrolidinyl, morpholinyl, or tetrahydroisoquinolinyl;

Q represents phenyl or phenyl substituted by one or more substituents selected from the group consisting of alkyl C1 to 6, alkoxy C1 to 6, trifluoromethyl, halogen, nitro and cyano;

m and n independently represents an integer 0 to 5;

and pharmaceutically acceptable salts thereof.

We prefer that T represents $—U—(CH_2)_a—N(X)—(CH_2)_b—$. We particularly prefer that T represents $—U—(CH_2)_a—N(X)—(CH_2)_b—$ and U represents $CH_2$. We especially prefer that T represents $—U—(CH_2)_a—N(X)—(CH_2)_b—$, U represents $CH_2$ and a and b each represent 1.

We prefer that D represents alkyl C1 to 3, particularly methyl or ethyl, especially ethyl.

When T represents $—U—(CH_2)_a—N(X)—(CH_2)_b—$, we prefer that X represents hydrogen, methyl or the group $—CH_2Q$.

When T represents a $C_{3-5}$ saturated or unsaturated alkylene chain substituted by $—(CH_2)_m—NXY$ or $—O—(CH_2)_2—NH—$ substituted by $—(CH_2)_m—NXY$, we prefer X and Y independently to represent hydrogen, methyl or the group $—CH_2Q$, although it is not preferred that X and Y both represent the group $—CH_2Q$. We particularly prefer that one of X and Y represents hydrogen or methyl and the other represents the group $—CH_2Q$.

We prefer that n represents 1.

We prefer Q to represent phenyl or phenyl substituted by a substituent selected from the group consisting of alkyl C1 to 6, alkoxy C1 to 6, trifluoromethyl, halogen, nitro and cyano. We particularly prefer that Q represents phenyl or phenyl substituted by alkyl C1 to 6 or halogen.

According to the invention, there is also provided a process for the preparation of compounds of formula I and pharmaceutically acceptable salts thereof, which comprises (a) preparing a compound of formula I in which X or at least one of X and Y represents alkyl C1 to 6 or the group $—(CH_2)_nQ$, by reacting a corresponding compound of formula I in which X or one or both of X and Y represents hydrogen, with a compound of formula II $$R^1—L \qquad II$$

wherein $R^1$ represents alkyl C1 to 6 or the group $—(CH_2)_nQ$ and L is a leaving group, or (b) preparing a compound of formula I in which T represents a $C_{3-5}$ saturated or unsaturated alkylene chain substituted by $—(CH_2)_m—NXY$ or $—O—(CH_2)_2—NH—$ substituted by $—(CH_2)_m—NXY$ by reaction of a corresponding compound in which T represents a $C_{3-5}$ saturated or unsaturated alkylene chain substituted by $—(CH_2)_m—L$ or $—O—(CH_2)_2—NH—$ substituted by $—(CH_2)_m—L$ and L represents a leaving group, with a compound of formula III $$XYNTH \qquad III$$

wherein X and Y are as defined above, or (c) reacting a compound of formula IV

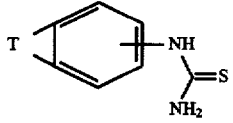

wherein T is as defined above, with a compound of formula V $$D—L \qquad V$$

wherein D is as defined above and L is a leaving group, and where necessary or desired converting the resulting compound into a pharmaceutically acceptable salt thereof or vice versa as described below.

In processes (a) and (b), the reactions will take place under standard conditions, for example by reacting the two materials in an inert solvent under basic conditions at room temperature for a period of up to 12 hours. We have frequently found it desirable to treat the amine with NaH before reacting with the other compound. Suitable leaving groups L include thioalkyl, sulphonic acid, trifluorocarbon sulphonic acid, halide, alkyl and aryl alcohols and tosyl groups; others are recited in 'Advanced Organic Chemistry', J. March (1985) 3rd Edition, McGraw-Hill on page 315 and are well known in the art. We prefer that L represents halide, particularly bromide.

In process (c) the reaction will proceed on combining the two reactants in an inert solvent e.g. acetone. Suitable leaving groups that L may represent include thioalkyl, sulphonic acid, trifluorocarbon sulphonic acid, halide, alkyl and aryl alcohols and tosyl groups; others are recited in 'Advanced Organic Chemistry', J. March (1985) 3rd Edition, McGraw-Hill on page 315 and are well known in the art. We prefer to use the iodide, toluenesulphonate or methane sulphonate derivative.

Compounds of formula IV may be prepared following the method of Rasmussen et al in Synthesis (1988) 456–459. Compounds of formula III can thus be prepared by reacting a compound of formula VI

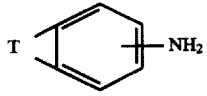

VI wherein T is as defined above, with benzoyl isothiocyanate followed by aqueous-alkaline cleavage of the resultant benzoylthiourea derivative.

The compounds of formula VI, may be prepared by reduction of a corresponding compound of formula VII,

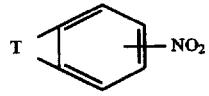

VII wherein T is as defined above.

The reduction reaction may be performed under a number of conditions, for example those described in J March "Advanced Organic Chemistry" 3rd Edition (1985) on pages 1103–1104. These include catalytic hydrogenation, use of Zn, Sn or Fe metal, $AlH_3$—$AlCl_3$, sulphides and others. We prefer to perform the reaction by hydrogenation at atmospheric pressure in the presence of a palladium and carbon catalyst for typically 1–4 hours, or until reduction is complete.

Compounds of formula VII in which T is as defined above and X or at least one of X and Y represents alkyl C1 to 6 or the group —$(CH_2)_n$Q, may be prepared by reaction of a corresponding compound of formula VII in which X and/or Y represents hydrogen with a compound of formula II.

This reaction may be performed under conditions analogous to those described above in process (a).

Compounds of formula VII in which T represents a $C_{3-5}$ saturated or unsaturated alkylene chain substituted by —$(CH_2)_m$—NXY or —O—$(CH_2)_2$—NH— substituted by —$(CH_2)_m$—NXY may be prepared by reaction of a corresponding compound in which T represents a $C_{3-5}$ saturated or unsaturated alkylene chain substituted by —$(CH_2)_m$—L or —O—$(CH_2)_2$—NH— substituted by —$(CH_2)_m$—L and L represents a leaving group, with a compound of formula III.

This reaction may be performed under conditions analogous to those described above in process (b).

Compounds of formula VII in which X represents hydrogen are either known or may be prepared by known methods. For example, they may be prepared by nitration of the unnitrated derivative. This nitration reaction conventionally takes place on reacting the unnitrated aromatic compound with nitric acid either alone or in water, acetic acid, acetic anhydride or sulphuric acid. Further details of these reactions and further alternative reagents are set out in J March "Advanced Organic Chemistry" 3rd Edition (1985) on pages 468–470.

Compounds of formula II, III and V are either known or may be prepared by conventional methods known per se.

Compounds of formula I may be prepared as such, or as acid addition salts of the type described above. Alternatively, they may be prepared as a non-pharmaceutically acceptable addition salt, for example a salt of oxalic acid, and any product thereof may subsequently be converted to a pharmaceutically acceptable salt by conventional means.

Salts of compounds of formula I may be formed by reacting the free acid, base or a salt thereof, with one or more equivalents of the appropriate base or acid. The reaction may be carried out in a solvent or medium in which the salt is insoluble or in a solvent in which the salt is soluble, eg water, dioxan, ethanol, tetrahydrofuran or diethyl ether, or a mixture of solvents, which may be removed in vacuo or by freeze drying. The reaction may be a metathetical process or it may be carried out on an ion exchange resin.

Where necessary, amine or other reactive groups may be protected using a protecting group as described in the standard text "Protecting groups in Organic Synthesis", 2nd Edition (1991) by Greene and Wuts. Amine-protecting groups which may be mentioned in particular include alkyloxycarbonyl C2 to 7, eg t-butyloxycarbonyl, phenylalkyloxycarbonyl C8 to 13, eg benzyloxycarbonyl. However, it is preferred to protect amine groups by treatment with trifluoroacetic anhydride in a suitable solvent (e.g. methylene chloride, methanol) at room temperature. Deprotection can be achieved by hydrolysis in water.

The compounds of the invention and intermediates may be isolated from their reaction mixtures by standard techniques.

The term "alkyl C1 to 6" includes straight chain, branched, saturated, unsaturated, aliphatic and cyclic alkyl containing 1 to 6 carbon atoms. "Alkyl C1 to 3" may be interpreted similarly.

The compounds of formula I may exist in enantiomeric forms. The various optical isomers may be isolated by separation of a racemic mixture of the compounds using conventional techniques, e.g. fractional crystallisation, or HPLC. Alternatively the individual enantiomers may be made by reaction of the appropriate optically active starting materials under reaction conditions which will not cause racemisation.

Intermediate compounds may also exist in enantiomeric forms and may be used as purified enantiomers, diastereomers, racemates or mixtures.

The compounds of general formula I possess useful pharmacological activity in animals. In particular, they possess useful nitric oxide synthase inhibiting activity, and are expected to be useful in the treatment or prophylaxis of human diseases or conditions in which the synthesis or oversynthesis of nitric oxide forms a contributory part; for example, hypoxia, e.g. in cases of cardiac arrest, stroke and neonatal hypoxia, neurodegenerative conditions including nerve degeneration and/or nerve necrosis in disorders such as ischaemia, hypoxia, hypoglycemia, epilepsy, and in external wounds (such as spinal cord and head injury), hyperbaric oxygen convulsions and toxicity, dementia e.g. pre-senile dementia, Alzheimer's disease and AIDS-related dementia, Sydenham's chorea, Parkinson's disease, Huntington's disease, Amyotrophic Lateral Sclerosis, Korsakoff's disease, imbecility relating to a cerebral vessel disorder, sleeping disorders, schizophrenia, anxiety, depression, seasonal affective disorder, jet-lag, depression or other symptoms associated with Premenstrual Syndrome (PMS), anxiety and septic shock. Compounds of formula I may also be expected to show activity in the prevention and reversal of tolerance to opiates and diazepines, treatment of drug addiction, relief of pain and treatment of migraine and other vascular headaches. The compounds of the present invention may also show useful immunosuppressive activity, be useful in the treatment or prophylaxis of inflammation, in the treatment of of gastrointestinal motility disorders, and in the induction of labour. The compounds may also be useful in the treatment of cancers that express nitric oxide synthase.

Compounds of formula I are expected to be particularly useful in the treatment or prophylaxis of neurodegenerative conditions or of migraine or for the prevention and reversal of tolerance to opiates and diazepines or for the treatment of drug addiction and especially in the treatment or prophylaxis of neurodegenerative disorders. We are particularly interested in conditions selected from the group consisting of hypoxia, ischaemia, stroke and Amyotrophic Lateral Sclerosis.

Thus according to a further aspect of the invention we provide the use of a compound of formula I or a pharmaceutically acceptable salt thereof as a pharmaceutical.

According to another feature of the invention we provide the use of a compound of formula I, or a pharmaceutically acceptable salt thereof, in the manufacture of a medicament for the treatment or prophylaxis of the aforementioned diseases or conditions; and a method of treatment or prophylaxis of one of the aforementioned diseases or conditions which comprises administering a therapeutically effective amount of a compound of formula I, or a pharmaceutically acceptable salt thereof, to a person suffering from or susceptible to such a disease or condition.

For the above mentioned therapeutic indications, the dosage administered will, of course, vary with the compound employed, the mode of administration and the treatment desired. However, in general, satisfactory results are obtained when the compounds are administered to a human at a daily dosage of the solid form of between 1 mg and 2000 mg per day.

The compounds of formula I, and pharmaceutically acceptable derivatives thereof, may be used on their own, or in the form of appropriate medicinal preparations for enteral or parenteral administration.

According to the invention, there is provided a pharmaceutical composition comprising preferably less than 80% and more preferably less than 50% of a compound of formula I, or a pharmaceutically acceptable salt thereof, in admixture with a pharmaceutically acceptable diluent or carrier.

We also provide a method of preparation of such a pharmaceutical formulation which comprises mixing the ingredients.

Examples of such diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include: tablets, capsules and dragees; sustained release compositions include those in which the active ingredient is bound to an ion exchange resin which is optionally coated with a diffusion barrier to modify the release properties of the resin.

We prefer the composition to contain up to 50% and more preferably up to 25% by weight of the compound of formula 1, or a pharmaceutically acceptable derivative thereof.

The enzyme nitric oxide synthase has a number of isoforms and compounds of formula I, and pharmaceutically acceptable salts thereof, may be screened for nitric oxide synthase inhibiting activity by procedures based on those of Bredt and Snyder in Proc. Natl. Acad. Sci. (1990) 87, 682–685 and Förstermann et. al., Eur. J. Pharm. (1992) 225, 161–165 as follows. Nitric oxide synthase converts $^3$H-L-arginine to $^3$H-L-citrulline which can be separated by cation exchange chromatography and quantified by scintillation counting.

Screen A (A) Screen for neuronal nitric oxide synthase inhibiting activity

Enzyme was isolated from rat hippocampus or cerebellum. The cerebellum or hippocampus of a male Sprague-Dawley rat (250–275 g) is removed following $CO_2$ anaesthesia of the animal and decapitation. Cerebellar or hippocampal supernatant is prepared by homogenisation in 50 mM Tris-HCl with 1 mM EDTA buffer (pH 7.2 at 25° C.) and centifugation for 15 minutes at 20,000 g. Residual L-arginine is removed from the supernatant by chromatography through Dowex AG-50W-X8 sodium form and hydrogen form columns successively, and further centrifugation at 1000 g for 30 seconds.

For the assay, 25 μl of the final supernatant is added to each of 96 wells (of a 96 well filter plate) containing 25 μl L-arginine solution (of concentration 18 μM $^1$H-L-arginine, 96 nM $^3$H-L-arginine) and either 25 μl of an assay buffer (50 mM HEPES, 1 mM EDTA, 1.5 mM $CaCl_2$, pH 7.4) or 25 μl of test compound in the buffer at 22° C. To each test tube is added 25 μl of complete assay buffer (50 mM HEPES, 1 mM EDTA, 1.5 mM $CaCl_2$, 1 mM DTT, 100 μM NADPH, 10 μg/ml calmodulin, pH 7.4) to initiate the reaction and the reaction is stopped after 10 minutes by addition of 200 μl of a slurry of termination buffer (20 mM HEPES, 2 mM EDTA, pH 5.5) and Dowex AG-50W-X8 200–400 mesh.

Labelled L-citrulline is separated from labelled L-arginine by filtering each filter plate and 75 ul of each terminated reaction is added to 3 ml of scintillation cocktail. The L-citrulline is then quantified by scintillation counting.

In a typical experiment using the cerebellar supernatant, basal activity is increased by 20,000 dpm/ml of sample above a reagent blank which has an activity of 7,000 dpm/ml. A reference standard, N-nitro-L-arginine, which gives 80% inhibition of nitric oxide synthase at a concentration of 1 μM, is tested in the assay to verify the procedure.

Screen B (B) Screen for inducible nitric oxide synthase inhibiting activity

Enzyme is prepared, after induction, from the cultured human colorectal carcinoma cell line, DLD-1 (obtained from the European Collection of Animal Cell Cultures) DLD-1 cells are cultured in RPMI 1640 media supplemented with 10% foetal bovine serum, 4 mM L-glutamine and antibiotics (100 units/ml penicillin G, 100 μg/ml streptomycin & 0.25 μg/ml amphotericin B) and 100 ug/ml kanamycin. Cells are routinely grown in 225 $cm^3$ flasks containing 35 ml medium kept at 37° C. and in a humidified atmosphere containing 5% $CO_2$.

Nitric oxide synthase is produced by cells in response to interferon-about 250 U/ml IL-1, 1000 U/ml IFNγ, 200 U/ml IL-6, and 200 U/ml TNF-alpha. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 μM dithiothreitol and a cocktail of protease inhibitors comprising leupeptin (2 μg/ml), soy bean trypsin inhibitor (10 μg/ml), aprotinin (5 μg/ml) & phenylmethylsulphonyl fluoride (50 μg/ml).

For the assay, 25 μl substrate cocktail (50 mM Tris-HCl (pH 7.5 at 20° C.), 400 μM NADPH, 20 μM flavin adenine dinucleotide, 20 μM flavin mononucleotide, 4 μM tetrahydrobiopterin, 12 μM L-arginine and 0.025 μCi L-[$^3$H] arginine) is added to wells of a 96 well filter plate (0.45 μM pore size) containing 25 μl of a solution of test compound in 50 mM Tris-HCl. The reaction is started by adding 50 μl of cell lysate (prepared as above) and after incubation for 1 hour at room temperature is terminated by addition of 50 μl of an aqueous solution of 3 mM nitroarginine and 21 mM EDTA.

Labelled L-citrulline is separated from labelled L-arginine using Dowex AG-50W. 150 μl of a 25% aqueous slurry of Dowex 50W (Na$^+$ form) is added to the assay after which the whole is filtered into 96 well plates. 70 μl of filtrate is sampled and added to wells of 96 well plates containing solid scintillant. After allowing the samples to dry the L-citrulline is quantified by scintillation counting.

In a typical experiment basal activity is 300 dpm per 70 μl sample which is increased to 1900 dpm in the reagent controls. Aminoguanidine, which gives an IC$_{50}$ (50% inhibitory concentration) of 10 μM, is tested as a standard to verify the procedure.

Screen C (C) Screen for endothelial nitric oxide synthase inhibiting activity

Enzyme may be isolated from human umbilical vein endothelial cells (HUVECs) by a procedure based on that of Pollock et al (1991) Proc. Nat. Acad. Sci., 88, 10480–10484. HUVECs were purchased from Clonetics Corp (San Diego, Calif., U.S.A.) and cultured to confluency. Cells can be maintained to passage 35–40 without significant loss of yield of nitric oxide synthase. When cells reach confluency, they are resuspended in Dulbecco's phosphate buffered saline, centrifuged at 800 rpm for 10 mins, the cell pellet homogenised in ice-cold 50 mM Tris-HCl, 1 mM EDTA, 10% glycerol, 1 mM phenylmethylsulphonylfluoride, 2 μM leupeptin at pH 4.2. Following centrifugation at 34,000 rpm for 60 mins, the pellet is solubilised in the homogenisation buffer which also contains 20 mM CHAPS. After a 30 min incubation on ice, the suspension is centrifuged at 34,000 rpm for 30 mins. The resulting supernatant is stored at –80° C. until use.

For the assay, 25 μl of the final supernatant is added to each well of a 96 well filter plate containing 25 μl L-arginine solution (of concentration 12 μM $^1$H-L-arginine, 64 nM $^3$H-L-arginine) and either 25 μl of an assay buffer (50 mM HEPES, 1 mM EDTA, 1.5 mM CaCl$_2$, pH 7.4) or 25 μl of test compound in the buffer at 22° C. To each well was added 25 μl of complete assay buffer (50 mM HEPES, 1 mM EDTA, 1.5 mM CaCl$_2$, 1 mM DTT, 100 μM NADPH, 10 μg/ml calmodulin, 12 μM tetrahydrobiopterin, pH 7.4) to initiate the reaction and the reaction is stopped after 30 mins by addition of 200 ul of a 50% slurry of termination buffer (20 mM HEPES, 2 mM EDTA, pH 5.5) and Dowex AG-50W-X8 200–400 mesh.

Labelled L-citrulline is separated from labelled L-arginine by filtration into another 96 well plate and 75 ul of each terminated reaction is added to 3 ml of scintillation cocktail. The L-citrulline is then quantified by scintillation counting.

In a typical experiment, basal activity is increased by 5,000 dpm/ml of sample above a reagent blank which has an activity of 1500 dpm/ml. A reference standard, N-nitro-L-arginine, which gives 70–90% inhibition of nitric oxide synthase at a concentration of 1 μM, is tested in the assay to verify the procedure.

Compounds may also be tested in an ex-vivo assay to determine the extent of brain penetration.

Screen D (D) Ex vivo assay for neuronal nitric oxide synthase inhibiting activity Male Sprague-Dawley rats (250–275 g) were dosed intravenously at 10 mg/kg with test compound dissolved in 0.9% saline or with saline alone as control. At a predetermined time (typically 2–24 hours) after treatment, the animals were sacrificed, the cerebellum removed and the supernatant prepared and assayed for nitric oxide synthase activity as described in Screen A.

As a further confirmatory test, a fraction of the cerebellar supernatant was applied to a 2'-5'-ADP Sepharose column (which binds nitric oxide synthase) and subsequently eluted with NADPH. The eluant was tested for nitric oxide synthase activity following the procedure of Screen A Compounds that penetrate the rat brain and inhibit neuronal nitric oxide synthase resulted in reduced nitric oxide synthase activity both in the supernatant preparation and in the eluant from the 2'-5'-ADP Sepharose column.

In the screens for nitric oxide synthase inhibition activity, compound activity is expressed as IC$_{50}$ (the concentration of drug substance which gives 50% enzyme inhibition in the assay). IC$_{50}$ values for test compounds were initially estimated from the inhibiting activity of 1, 10 and 100 μM solutions of the compounds. Compounds that inhibited the enzyme by at least 50% at 10 μM were retested using more appropriate concentrations so that an IC$_{50}$ could be determined.

In Screen A above (a screen for activity against the neuronal isoform of nitric oxide synthase), the compound of Example 1 below gave an IC$_{50}$ of less than 10 μM indicating that it is expected to show useful therapeutic activity. In Screens B and C (the screens for activity against the macrophage and endothelial isoforms of nitric oxide synthase) the compound of Example 1 gave IC$_{50}$ values more than 10 times that obtained in Screen A indicating that it shows desirable selectivity.

The compounds of Example 2 was also tested in Screen A and also gave an IC$_{50}$ value of less than 10 μM. Thus this compound is also expected to show useful therapeutic activity.

When compared with compounds of the prior art, the compounds of formula I, and pharmaceutically acceptable salts thereof, have the advantage that they may be less toxic, be more efficacious, be longer acting, have a broader range of activity, be more potent, be more selective for the neuronal isoform of nitric oxide synthase enzyme, produce fewer side effects, be more easily absorbed or have other useful pharmacological properties.

The invention is illustrated, but in no way limited, by the following examples:

EXAMPLE 1

N-(1,2,3,4-tetrahydroisoquinolin-7-yl)carbamimidothioic acid ethyl ester (a) 2-(7-amino-1,2,3,4-tetrahydroisoquinoline)2,2,2-trifluoroacetamide To a solution of 4.21 g (23.6 mmol) of 7-nitro-1,2,3,4-tetrahydroisoquinoline and 3.6 mL 926 mmol) of triethylamine in 100 mL of methylene chloride at 0° C. was added 3.5 mL (25 mmol) of trifluoroacetic anhydride. the reaction mixture was stirred overnight. The reaction mixture was extracted with dilute hydrochloric acid. The aqueous phase was basified and extracted with methylene chloride. The dried organic phase (magnesium sulfate) was to give N-(7-nitro-1,2,3,4-tetrahydroisoquinoline)trifluoroacetamide as a yellow solid. This compound was immediately taken up in 200 mL of ethanol, 0.50 g of 5% palladium on carbon was added, and the mixture was hydrogenated on a Parr Hydrogenator at 45 psi for 1.5 h. The catalyst was removed by filtration and the solvent was evaporated. The residue was triturated with 100 mL of petroleum ether to give 5.45 g (95%) of the title compound as a grey solid, m.p. 61°–3° C.

(b) 1,2,3,4-tetrahydroisoquinolin-7-thiourea

To a solution of 1.3 mL (9.7 mmol) of benzoyl isothiocyanate in 13 mL of acetone at reflux was added rapidly 1.25 g (5.12 mmol) of 2-(7-amino-1,2,3,4-tetrahydroisoquinoline)trifluoroacetamide at such a rate to control reflux. After addition was complete, the reaction mixture was stirred for 3 h. Upon cooling, the solid was collected and washed with 30 mL of acetone to give 1.74 g (83%) of the intermediate 1-benzoyl-3-[2-(2-2-2-trifluoroacetamide)1,2,3,4-tetrahydroisoquinolin-7-thiourea as an off-white solid. This compound was immediately added to 20 mL of a 5% sodium hydroxide solution and the resulting solution was heated at 80° C. for 1 h. Upon cooling to ambience, the solution was filtered to give 0.78 g (74%) of the title compound, m.p. 198°–203° C.

(c) N-(1,2,3,4-tetrahydroisoquinolin-7-yl)carbamimidothioic acid ethyl ester

To a suspension of 0.75 g (3.61 mmol) of 1,2,3,4-tetrahydroisoquinolin-7-thiourea in 10 mL of isopropanol was added 0.35 g (3.7 mmol) of methanesulfonic acid in 2 mL of isopropanol. The reaction mixture was stirred for 0.25 h before 0.85 mL (8.4 mmol) of ethyl methanesulfonate. The reaction mixture was heated at reflux for 4 h. The solvent was stripped in vacuo to give an oil which was dissolved in 100 mL of water. the aqueous phase was made basic with saturated sodium bicarbonate and the aqueous phase was extracted 8 times with 100 mL of methylene chloride. The combined extracts were dried over magnesium sulfate and concentrated to give 0.61 g of an oil which solidified on standing. Column chromatography on silica gel using 10% methanol in chloroform saturated with ammonia afforded 0.45 g (53%) of the title compound as a white solid, MS 236 (M+H).

EXAMPLE 2
N-5-(2-(((3-chlorophenyl)methyl)(methyl)amino)indanyl) carbamimidothioic acid, ethyl ester (a) 2-((3-Chlorophenyl)carbonyl)amino-5-nitroindane To 2-amino-5-nitroindane hydrochloride (1.5 g, 7.0 mmol) in methylene chloride (50 ml) at 0° C. was added triethylamine (2.1 ml, 15.0 mmol) followed by 3-chlorobenzoyl chloride (1.0 ml, 7.5 mmol). The mixture was dumped immediately into water and the layers separated. The aqueous layer was extracted with methylene chloride (2×20 ml) and the combined extracts washed with water, dried over MgSO$_4$, filtered, and concentrated to an oil which was homogeneous by TLC and used immediately in the next step: M.S. (M+H)$^+$=317.

(b) 2-((3-Chlorophenyl)methyl)amino-5-nitroindane

To 2-((3-chlorophenyl)carbonyl)amino-5-nitroindane (2.2 g, 7.0 mmol) in THF (75 ml) was added BH$_3$•THF (1.0M, 35 ml, 35 mmol) dropwise. The mixture was refluxed for 12 hr, cooled to 0° C., quenched with 4N HCl (60 ml), and refluxed for 1 hr. The resulting solution was evaporated to an oil, made basic with 50% NaOH, and extracted with methylene chloride (3×20 ml). The combined extracts were washed with water, dried over MgSO$_4$, filtered and concentrated to an oil. Treatment with IPA/HCl yielded 2-((3-chlorophenyl)methyl)amino-6-nitroindane: (2.1 g, 88% two steps); m.p. 234°–237° C.

(c) 2-((3-chlorophenyl)methyl)(methyl)amino-5-nitroindane

To 2-((3-chlorophenyl)methyl)amino-5-nitroindane (4.4 g, 14.5 mmol) in formic acid (5.5 ml) was added formaldehyde (12 ml). The mixture was heated to reflux for 30 minutes, cooled, neutralized with 2N NaOH, and extracted with ethyl acetate (3×70 ml). The combined extracts were washed with water, dried over MgSO$_4$, filtered, and concentrated to an oil: (4.2 g, 91%); M.S. (M+H)$^+$=317.

(d) 2-((3-chlorophenyl)methyl)(methyl)amino-5-aminobenzene

To 2-((3-chlorophenyl)methyl)(methyl)amino-5-nitroindane (4.3 g, 13.6 mmol) in 85% AcOH/H$_2$O (100 ml) was added zinc metal (7.1 g, 109.0 mmol). The mixture was stirred for 5 min, filtered through celite, and evaporated to an oil. The oil was dumped into basic water and extracted with ethyl acetate (3×100 ml). The combined extracts were washed with water, dried over MgSO$_4$, filtered, and concentrated to an oil: (3.6 g, 92%); M.S. (M+H)$^+$=287.

(e) 5-(2-(((3-chlorophenyl)methyl)(methyl)amino)indanyl)-1-benzoyl-2-thiourea

To a solution of benzoyl isothiocyanate (2.7 g, 16.5 mmol) in 15 ml of dry acetone, preheated to a very gentle reflux, was added rapidly, at a rate as to control a vigorous reflux, 2-((3-chlorophenyl)methyl)(methyl)amino-5-aminobenzene (3.6 g, 12.4 mmol) dissolved in 10 ml of dry acetone. The reaction mixture was refluxed for 30 minutes, poured onto ice with vigorous stirring, and extracted with ethyl acetate (3×100 ml). The combined extracts were washed with water, dried over MgSO$_4$, filtered, and concentrated to a solid which was recrystallized from IPA: (3.12 g, 58%); m.p. 128°–130° C.

(f) 5-(2-(((3-chlorophenyl)methyl)(methyl)amino)indanyl)-2-thiourea

A mixture of 5-(2-(((3-chlorophenyl)methyl)(methyl) amino)indanyl)-1-benzoyl-2-thiourea (3.1 g, 7.12 mmol) and 40 ml of 2.5N aqueous sodium hydroxide was heated at 90° C. for 35 minutes with stirring. Poured the warm reaction mixture into 60 ml of water with stirring. The product was extracted into three portions of methylene chloride. The combined extracts were washed with water, dried over magnesium sulfate and concentrated to dryness. The residue was chromatographed over silica gel (8:1 ethyl acetate/hexane)and concentrated to an oil: (2.2 g, 93%); M.S. (M+H)$^+$=246.

(g) N-5-(2-(((3-chlorophenyl)methyl)(methyl)amino) indanyl)carbamimidothioic acid, ethyl ester 5-(2-(((3-chlorophenyl)methyl)(methyl)amino)indanyl)-2-thiourea (2.2 g, 6.33 mmol) was suspended in 20 ml of 200 ethanol, and the mixture was treated with 0.41 ml of methanesulfonic acid, and the n 1.35 ml of ethyl methanesulfonate. The mixture was refluxed for 4 hr, evaporated, made basic with saturated bicarbonate, and extracted with methylene chloride (3×30 ml). The combined extracts were washed with water, dried over MgSO$_4$, filtered, and concentrated to a oil which was dissolved in ethyl acetate and treated with IPA/HCl. The solids were filtered and washed with IPA: (2.40 g, 83%); m.p. dec >150° C.

EXAMPLE 3
N-(2-methyl-1,2,3,4-tetrahydroisoquinolin-7-yl) carbamimidothioic acid ethyl ester dihydrochloride (a) 7-nitro-2-methyl-1,2,3,4-tetrahydroisoquinoline hydrochloride A solution of 4.00 g (18.7 mmol) of 7-nitroisoquinoline in 10 ml of formic acid and 17 ml of 38% aqueous formaldehyde was heated at reflux for 1 h. The reaction mixture was cooled, poured onto ice and basified with aqueous ammonia. The gummy residue which precipitated was extracted twice with methylene chloride. The dried (magnesium sulfate) organic phase was concentrated to give crude 7-nitro-2-methyl-1,2,3,4-tetrahydroisoquinoline as a thick oil. This oil was immediately taken up in ethanol (50 ml) and a solution of hydrochloric acid in ethanol was added until the solution was distinctly acidic to litmus. Ether was added to induce precipitation and the resulting solid was collected to give 3.99 g (93%) of the title compound as a yellow solid, m.p. 236°–8° C. (dec).

(b) 7-amino-2-methyl-1,2,3,4-tetrahydroisoquinoline hydrochloride

A suspension of 3.98 g (17.5 mmol) of 7-nitro-2-methyl-1,2,3,4-tetrahydroisoquinoline hydrochloride and 0.4 g of 10% palladium on carbon in 200 ml of ethanol was hydrogenated at 50 psi for 2 h. The catalyst was filtered and washed with a small amount of water. The filtrate was concentrated yielding an aqueous solution. Absolute ethanol was added and evaporated driving off the excess water until a solid was produced. This solid was dissolved in hot ethanol (60 ml) and ether was added slowly to induce crystallization. The product was collect to give 3.38 g (97%) of the title compound as an off-white solid, m.p. 114°–9° C.

(c) 2-methyl-1,2,3,4-tetrahydroisoquinolin-7-thiourea

A solution of 3.88 g (19.5 mmol) of 7-amino-2-methyl-1,2,3,4-tetrahydroisoquinoline hydrochloride in 100 ml of water was made basic with potassium carbonate solution and was extracted twice with methylene chloride. The dried (magnesium sulfate) organic phase was concentrated to give 3.13 g (99%) of the free base as an oil. This oil was taken up in acetone (75 ml) and 2.21 g (19.4 mmol) of trifluoroacetic acid in 100 ml of acetone was added. The solution was heated to reflux where 5.2 ml (39 mmol) of benzyl isothiocyanate was added dropwise. The reaction mixture was heated for 1 h before cooling to ambience. The solvent was removed in vacuo and the resulting oil was taken up in methanol (150 ml) and 2.5M sodium hydroxide (50 ml). This solution was heated at 65° C. for 1 h before cooling to ambient temperature. The methanol was stripped in vacuo and the aqueous solution was cooled to precipitate the product. The solid was collected to give 2.22 g of the title compound as a light yellow solid, m.p. 184°–6° C. A second crop of the title compound (0.79 g, total yield 69%) was also obtained.

(d) N-(2-methyl-1,2,3,4-tetrahydroisoquinolin-7-yl) carbamimidothioic acid ethyl ester dihydrochloride To a suspension of 0.88 g (4.0 mmol) of 2-methyl-1,2,3, 4-tetrahydroisoquinolin-7-thiourea in 8 ml of isopropanol was added 0.39 g (3.9 mmol) of methanesulfonic acid. The solution was heated at reflux for 0.5 h to ensure formation of the methanesulfonate salt as both the salt and free base were insoluble in isopropanol. To this solution was added 1.5 ml (14 mmol) of ethyl methanesulfonate and heating was continued overnight affording a clear solution. The solvent was removed in vacuo and the resulting oil was taken up in water, basified with potassium carbonate and extracted twice with methylene chloride. The dried (magnesium sulfate) organic phase was concentrated to give an oil. This oil was taken up in ethanol and acidified with hydrochloric acid in ethanol until distinctly acidic to litmus. Ether was added and the salt came out as a viscous oil. The solvent was decanted and the oil was washed several times with ether. The oil was taken up in water (250 ml) and the solution was treated with decolorizing carbon. The solution was filtered and the filtrate was diluted to 500 ml with water. This solution was freeze-dried to give 1.06 g (78%) of the title compound as a monohydrate. MS(CI) 250 (M+H); NMR (DMSO/D2O) 7.33 (d, 1H), 7.21 (d, 1H), 7.17 (s, 1H), 4.36 (broad s, 2H), 3.0–3.6 (m, 6H), 3.17 (s, 3H), 1.30 (t, 3H).

EXAMPLE 4

N-(2-methyl-1,2,3,4-tetrahydroisoquinolin-7-yl) carbamimidothioic acid methyl ester dihydrochloride To a suspension of 1.00 g (4.52 mmol) of 2-methyl-1,2, 3,4-tetrahydroisoquinolin-7-thiourea (Example 3, step (c)) in 10 ml of isopropanol was added 0.44 g (4.5 mmol) of methanesulfonic acid. The solution was stirred at ambient temperature for 2 h to ensure formation of the methanesulfonate salt as both the salt and free base were insoluble in isopropanol. To this solution was added 6.7 g (47 mmol) of methyl iodide and the reaction mixture was stirred overnight. The solvent was stripped in vacuo and the residue was dissolved in water, treated with decolorizing carbon and filtered to afford a clear, colorless, aqueous solution. This solution was made basic with potassium carbonate and extracted twice with methylene chloride. The organic phases were combined, dried (magnesium sulfate), and concentrated in vacuo to give 1.02 g (96%) of the product as a free base. This oil was taken up in ethanol and was made distinctly acidic by the addition of hydrochloric acid in ethanol. Addition of excess ether caused the salt to separate as an oil. The solvent was decanted and this oil was washed several times with ether. This oil was taken up in 250 ml of water and was again treated with decolorizing carbon. The solution was filtered and the filtrate was diluted to 500 ml with water. This solution was freeze-dried to give 0.70 g of the title compound as a white solid. MS (CI) 236 (M+H). NMR (DMSO/D2O) 11.6–11.9 (broad, 1H), 9.4–9.7 (broad, 1H), 7.36 (d, 1H), 7.24 (d, 1H), 7.18 (s, 1H), 4.2–4.6 (broad m, 2H), 3.0–3.7 (broad m, 4H), 2.87 (s, 3H), 2.70 (s, 3H).

I claim:

1. A compound of formula I

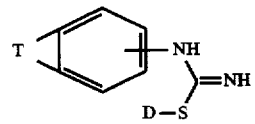

wherein

D represents alkyl C1 to 6;

T represents a $C_{3-5}$ saturated or unsaturated alkylene chain substituted by —(CH$_2$)$_m$—NXY; —O—(CH$_2$)$_2$—NH- substituted by —(CH$_2$)$_m$—NXY; or —U—(CH$_2$)$_a$—N(X)—(CH$_2$)$_b$—;

U represents NH, O or CH$_2$;

a and b, which may be the same or different, represent an integer 0 to 3, provided that a+b is in the range 1 to 3;

X and Y, which may be the same or different, represent hydrogen, alkyl C1 to 6, or a group —(CH$_2$)$_n$Q;

or NXY together represents piperidinyl, pyrrolidinyl, morpholinyl, or tetrahydroisoquinolinyl;

Q represents phenyl optionally substituted by alkyl C1 to 6, alkoxy C1 to 6, trifluoromethyl, halogen, nitro or cyano;

m and n independently represents an integer 0 to 5;

or a pharmaceutical acceptable salt thereof.

2. A compound of formula I, according to claim 1, wherein T represents —U—(CH$_2$)$_a$—N(X)—(CH$_2$)$_b$—.

3. A compound of formula I, according to claim 1 or claim 2, wherein T represents —U—(CH$_2$)$_a$—N(X)—(CH$_2$)$_b$— and U represents CH$_2$.

4. A compound of formula I, according to claim 1, wherein T represents —U—(CH$_2$)$_a$—N(X)—(CH$_2$)$_b$—, U represents CH$_2$ and a and b each represents 1.

5. A compound of formula I, according to claim 4, wherein D represents ethyl.

6. A compound of formula I, according to claim 1, which is:
N-(1,2,3,4-tetrahydroisoquinolin-7-yl)carbamimidothioic acid ethyl ester;
N-5-(2-(((3-chlorophenyl)methyl)(methyl)amino)indanyl) carbamimidothioic acid ethyl ester;
N-(2-methyl-1,2,3,4-tetrahydroisoquinolin-7-yl) carbamimidothioic acid ethyl ester;
N-(2-methyl-1,2,3,4-tetrahydroisoquinolin-7-yl) carbamimidothioic acid methyl ester;
or a pharmaceutically acceptable salt thereof.

7. A compound according to claim 6 for use as a pharmaceutical.

8. A pharmaceutical composition comprising a compound as claimed in claim 1 in admixture with a pharmaceutically acceptable diluent or carrier.

9. A process for the preparation of compounds of formula I, as defined in claim 1, and pharmaceutically acceptable salts thereof, which comprises (a) preparing a compound of formula I in which X or at least one of X and Y represents alkyl C1 to 6 or the group —(CH$_2$)$_n$Q, by reacting a corresponding compound of formula I in which X or one or both of X and Y represents hydrogen, with a compound of formula II

R$^1$—L           II wherein R$^1$ represents alkyl C1 to 6 or the group —(CH$_2$)$_n$Q and L is a leaving group; or (b) preparing a compound of formula I in which T represents a C$_{3-5}$ saturated or unsaturated alkylene chain substituted by —(CH$_2$)$_m$—NXY or —O—(CH$_2$)$_2$—NH— substituted by —(CH$_2$)$_m$—NXY by reaction of a corresponding compound in which T represents a C$_{3-5}$ saturated or unsaturated alkylene chain substituted by —(CH$_2$)$_m$—L or —O—(CH$_2$)$_2$—NH— substituted by —(CH$_2$)$_m$—L and L represents a leaving group, with a compound of formula III

XYNH           III wherein X and Y are as defined in claim 1; or (c) reacting a compound of formula IV

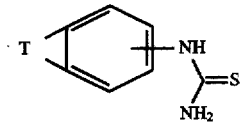

IV wherein T is as defined in claim 1, with a compound of formula V

D—L           V wherein D is as defined in claim 1 and L is a leaving group, and where necessary or desired converting the resulting compound into a pharmaceutically acceptable salt thereof or vice versa.

10. A method of treatment or prophylaxis of neurodegenerative disorders, or of tolerance to opiates or diazepines, or of drug addiction, which comprises administering to a patient in need thereof a therapeutically effective amount of a compound of the formula (I), as defined in claim 1, or a pharmaceutically acceptable salt thereof.

11. A compound of formula I, according to claim 1, wherein T represents a C$_{3-5}$ saturated or unsaturated alkylene chain substituted by (CH$_2$)$_m$—NXY.

* * * * *